(12) United States Patent
Wang

(10) Patent No.: US 10,149,737 B2
(45) Date of Patent: Dec. 11, 2018

(54) NITI ALLOY ROOT CANAL FILE WITH FLEXIBILITY GRADIENT AND MANUFACTURING METHOD THEREOF

(71) Applicant: SHENZHEN SUPERLINE TECHNOLOGY CO., LTD., Shenzhen (CN)

(72) Inventor: Zhong Wang, Shenzhen (CN)

(73) Assignee: SHENZHEN SUPERLINE TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 15/603,695

(22) Filed: May 24, 2017

(65) Prior Publication Data

US 2017/0290640 A1    Oct. 12, 2017

Related U.S. Application Data

(63) Continuation-in-part of application No. PCT/CN2016/079980, filed on Apr. 22, 2016.

(30) Foreign Application Priority Data

Apr. 12, 2016    (CN) .......................... 2016 1 0225401

(51) Int. Cl.
*A61C 5/42*    (2017.01)
(52) U.S. Cl.
CPC .......... *A61C 5/42* (2017.02); *A61C 2201/007* (2013.01)
(58) Field of Classification Search
CPC .......................... A61C 5/023; A61C 2201/007
See application file for complete search history.

(56) References Cited

U.S. PATENT DOCUMENTS 6,431,863 B1 *   8/2002   Sachdeva ................. A61C 5/42
                                                            433/102
7,648,599 B2 *   1/2010   Berendt ................... C22C 19/03
                                                            148/563

(Continued)

OTHER PUBLICATIONS

G. Xiaoju; "Preparation Technology and Latest Development of Functionally Gradient Materials", 2014, pp. 31-38, vol. 28, No. 1.

*Primary Examiner* — Ralph Lewis
(74) *Attorney, Agent, or Firm* — Muncy, Geissler, Olds & Lowe, P.C.

(57)    ABSTRACT

A NiTi alloy root canal file with a flexibility gradient, having a tip, middle portion and rear portion divided along the longitudinal direction. The internal microstructure of the tip is martensite, of the rear portion is austenite, and of the middle portion is a combination of martensite and austenite. The microstructure of martensite is continuously reduced and the microstructure of austenite is continuously increased as the distance from the tip increases. A manufacturing method for the NiTi alloy root canal file with a flexibility gradient. As the internal microstructure of the NiTi alloy root canal file with a flexibility gradient gradually changes along the axial direction and the strength also gradually changes, the flexibility and strength show a gradient change along the axial direction of the root canal file, providing excellent cutting property, high anti-fatigue life and significantly improving operation performance, safety, and life of the root canal files.

5 Claims, 7 Drawing Sheets

(56) References Cited

U.S. PATENT DOCUMENTS

| | | | |
|---|---|---|---|
| 8,916,009 B2* | 12/2014 | Ammon | A61C 5/023 148/563 |
| 2010/0092915 A1* | 4/2010 | Berendt | C22C 19/03 433/102 |
| 2011/0271529 A1* | 11/2011 | Gao | A61C 5/42 29/896.1 |

* cited by examiner

NITI ALLOY ROOT CANAL FILE WITH FLEXIBILITY GRADIENT AND MANUFACTURING METHOD THEREOF

CROSS-REFERENCE TO RELATED APPLICATIONS

This application is a Continuation-in-Part of co-pending Application No. PCT/CN2016/079980 filed on Apr. 22, 2016, for which priority is claimed under 35 U.S.C. § 120; and this application claims priority of Application No. 201610225401.6 filed in China on Apr. 12, 2016 under 35 U.S.C. § 119; the entire contents of all of which are hereby incorporated by reference.

BACKGROUND OF THE INVENTION

Technical Field

The present invention relates to dental instruments, and more especially, to a NiTi alloy root canal file with a flexibility gradient and the manufacturing method thereof.

Description of Related Art

Root canal files are the main instruments for thoroughly clearing the diseased inner wall of root canals, removing diseased tissues and shaping a complete and smooth inner cavity of root canals.

The structure of a root canal file consists of a working portion 1 which is provided with a helical cutting edge, a handle portion 2 and a stopping ring 3, and generally has a properly coned external profile, as shown in FIG. 1.

The root canal instrument makes a rotary motion in the root canal 4 at a certain speed during working to cut the internal surface of the root canal for the purpose of the root canal cleaning and shaping, as shown in FIG. 2. Due to an inversely conical curved structure, a root canal is often curved remarkably in the middle and lower portions, so the root canal file is subject to severe alternating bending deformation in operation.

To thoroughly clear the interior of the root canal, an ideal root canal file shall have flexibility with a gradient transition from the tip portion to the rear portion. Namely, a root canal file shall meet three requirements in working conditions: firstly, the tip of the root canal file shall have a certain flexibility to lead the root canal file to the bottom of the root canal smoothly, so that it can clean and shape the tip of the root canal, and meanwhile prevent the generation of steps and lateral perforation on the inner wall of the root canal; secondly, the root canal file shall have a certain cutting capacity so as to effectively remove diseased tissues and complete root canal shaping; thirdly, the root canal file shall have a long resistance-to-bending fatigue fracture life to prevent fracturing of the root canal file during use and further avoid medical accidents.

A traditional stainless steel root canal file features a good cutting property due to high strength, but high rigidity is prone to cause steps and lateral perforation on the inner surface of the root canal. The NiTi alloy, boasting excellent elasticity and bio-compatibility, is broadly applied in various medical instruments, including root canal files.

The NiTi alloy will undergo the phase transition between austenite A and martensite M under certain conditions, as shown in FIG. 3. As the temperature rises, the alloy begins to transform from martensite M to austenite A at the As temperature, and the transformation finishes at the Af temperature when the material has a 100% austenite A phase; as the temperature decreases, the alloy begins to transform from austenite A to martensite M at the Ms temperature, and the transformation finishes at the Mf temperature when the material has a 100% martensite M phase. The martensite M, which is transformed from austenite A due to the temperature drop, is called thermal martensite. Austenite A is of a cubic structure, while martensite M is of a monoclinic structure and the substructure of martensite M is a twin.

The twin substructure of the thermal martensite M is in a self-accommodative state. When the self-accommodative thermal martensite M in a twin state deforms, twins are re-oriented to form a single-oriented twin structure and materials exhibit excellent deformability and toughness, as shown in FIG. 4(*a*). When the NiTi alloy deforms in the austenite A state, austenite A will be induced to undergo the martensite phase transition under stress and finally transform into martensite M, and the alloy shows great deformation. The martensite generated under stress is known as stress-induced martensite. The stress-induced martensite M is unstable, and if the stress is removed, it will transform into the austenite A spontaneously and the NiTi alloy will recover its original shape. In this case, the NiTi alloy exhibits super-elasticity behaviors, as shown in FIG. 4(*b*).

The yield strength of the NiTi alloy varies with the temperature, as shown in FIG. 5, which is caused by the change in the internal microstructure of the alloy in different temperature intervals. In Temperature Interval I, the alloy has a microstructure of all thermal martensite M; in Temperature Interval II, the alloy has a microstructure of all austenite A; in Temperature Interval III, the alloy has a combined microstructure of martensite M and austenite A, and the microstructure of thermal martensite M in the alloy is continuously reduced and the microstructure of austenite A is continuously increased as the temperature increases.

The strength of the alloy varies with the temperature due to the change in the microstructure of the alloy. In Segment ab, the yield stress level of the NiTi alloy is relatively low and in this case the deformation mechanism is mainly the re-orientation of the twins of martensite M. In Segment bc, the yield stress of the NiTi alloy increases as the temperature increases, and the deformation in this stage is accomplished jointly by the re-orientation of the twins of martensite M and the transformation from austenite A to stress-induced martensite. In Segment cd, the deformation is accomplished by the yield deformation of austenite A.

Among the NiTi alloy root canal files disclosed at present, one type, made utilizing the super-elasticity property of the NiTi alloy, is called super-elastic NiTi alloy root canal files. The Af temperature of such a root canal file is designed below the temperature of 37° C. (human body environment temperature) when it is used, and the internal microstructure of the root canal file is all austenite A under the temperature of 37° C. when it is used. When the root canal file is bent and deformed under stress during use, martensite is induced under the stress inside the file. Once the stress is removed, stress-induced martensite M transforms back to austenite A, exhibiting super-elasticity behaviors, as shown in FIG. 4(*b*). With a high strength, such a root canal file has an excellent cutting property. However, the super-elastic NiTi alloy root canal file repeatedly undergoes periodic phase transition between stress-induced martensite M and austenite A internally during use. This phase transition can generate greater elastic strain, but some crystal defects such as dislocation are caused in the transformation between austenite A and martensite M. More and more crystal defects accumulate inside the material as the phase transition between austenite A and martensite M is repeated, which finally causes the root canal file to fracture, shortening the resistance-to-bending fatigue life of the NiTi alloy super-elastic root canal file and greatly affecting the use safety of the root canal file. The fracture generally occurs within 3-6 mm of the tip of the root canal file, because the tip portion of the root canal is severely curved.

Another type of NiTi alloy root canal file is known as a heat-activated root canal file. The Mf temperature of such a root canal file is designed higher than the temperature of 37° C. (human body environment temperature) when it is used, and the internal microstructure of the root canal file is all martensite M under the temperature of 37° C. when it is used. When the root canal file is bent and deformed under stress during use, martensite M inside undergoes re-orientation of the self-accommodative twin substructure to form a single-oriented twin structure and meanwhile the root canal file shows great deformation, as shown in FIG. 4(a). The root canal file can flexibly reach the tip portion of the root canal and provide good cleaning to the same since the low yield stress gives the root canal file excellent flexibility; besides, the deformation mechanism mainly depends on the re-orientation of self-accommodative martensite twins, so no crystal defect occurs in the repeated deformation, significantly prolonging the resistance-to-bending fatigue life of the heat-activated NiTi alloy root canal file. However, such a root canal file has relatively low strength, so its cutting property is relatively poor, and it is especially difficult to clean portions requiring a large amount of cutting such as the middle and upper portions of the root canal.

BRIEF SUMMARY OF THE INVENTION

To solve the problems in the prior arts, the present invention discloses a NiTi alloy root canal file with a flexibility gradient and the manufacturing method thereof which radically overcomes the deficiency of the NiTi alloy root canal files in the prior art to significantly improve the operation performance, safety and life of root canal files.

As described above, an ideal NiTi alloy root canal file at least meets three conditions simultaneously: an excellent cutting property, an excellent flexibility and a high anti-fatigue fracture property, but the three aspects contradict each other. An excellent cutting property means the root canal file requires high strength, while excellent flexibility requires the root canal file to have not very high strength and high resistance-to-bending fatigue fracture life requires the inside of the root canal file to have a microstructure of martensite or a combined microstructure of martensite and austenite. This is impossible for a NiTi alloy root canal file composed of a single phase. The super-elastic NiTi alloy root canal file as disclosed has an internal microstructure of austenite A, and the deformation in operation occurs as the phase transition between austenite A and martensite M is repeated. Such a root canal file has an excellent cutting property, but the tip portion of the root canal file is easy to fracture, causing the file to have low safety.

With regard to the NiTi alloy heat-activated root canal file already disclosed, its internal microstructure is martensite M, and the deformation in operation is accomplished by the re-orientation of self-accommodative martensite M. The root canal file has good flexibility and resistance-to-bending fatigue fracture life, but the strength of the alloy is relatively low and the cutting property is poor, and it is especially difficult to clean portions requiring a large amount of cutting such as the middle and upper portions of the root canal, causing the root canal file to have low operation performance.

The phase-transition temperature of the NiTi alloy can be controlled and adjusted by means of annealing. For the cold-deformed NiTi alloy with a high content of Ni, the microstructure recovers and the $Ti_3Ni_4$ phase particle is precipitated when heated, both of which work together to make the temperature of the alloy phase transition increase. FIG. 6 shows the law of change in its phase transition temperature with the annealing temperature after Ti-50.6 at % Ni alloy undergoes 30% cold deformation and then is annealed for 1 h at different temperatures.

The phase-transition temperature of the NiTi alloy is controlled and adjusted by means of annealing, which provides the possibility of both austenite A and martensite M in the same root canal.

The present invention discloses a NiTi alloy root canal file with a flexibility gradient, comprising a tip, a middle portion and a rear portion divided along its longitudinal direction, wherein the internal microstructure of the tip is martensite, the internal microstructure of the rear portion is austenite and the internal microstructure of the middle portion is a combined microstructure of martensite and austenite; the microstructure of martensite is continuously reduced and the microstructure of austenite is continuously increased as the distance from the tip increases.

The present invention also discloses a manufacturing method for the NiTi alloy root canal file with a flexibility gradient, wherein the super-elastic NiTi alloy wire with a high content of Ni in is taken as a raw material; root canal file blanks of a certain length are prepared using the raw material above; the root canal file blanks are subjected to a flexibility gradientization treatment in a flexibility gradientization unit to prepare root canal file blanks with a flexibility gradient; the root canal file blanks with a flexibility gradient are machined to prepare root canal file needles with a flexibility gradient; after the flexibility gradientization, the root canal file needle is mounted on a handle and a stopping ring to form a NiTi alloy root canal file with a flexibility gradient.

As a further improvement of the present invention, the flexibility gradientization unit comprises a heat conductor, an electric heater and a heat insulator, wherein the electric heater is provided in the heat insulator, the heat conductor is provided on the electric heater, a hole used for heating the root canal file blanks or the root canal file needles is made on the heat conductor, the lower portion of the heat conductor is snugly mounted with the electric heater, and the heat insulator encloses the heater and the lower portion of the heat conductor, so that a bottom-up gradient temperature field is formed in the heat conductor.

The present invention also discloses a manufacturing method for another NiTi alloy root canal file with a flexibility gradient, wherein the super-elastic NiTi alloy wire with a high content of Ni is taken as a raw material; the material is first machined to prepare the root canal file needles, and then the root canal file needle formed is inserted in a flexibility gradientization unit for treatment to prepare a root canal file needle with a flexibility gradient; the root canal file needle with a flexibility gradient is mounted on a handle and a stopping ring to form a NiTi alloy root canal file with a flexibility gradient.

As a further improvement of the present invention, the flexibility gradientization unit comprises a heat conductor, an electric heater and a heat insulator, wherein the electric heater is provided in the heat insulator, the heat conductor is provided on the electric heater, a hole used for heating the root canal file blanks or the root canal file needles is made on the heat conductor, the lower portion of the heat conductor is snugly mounted with the electric heater, and the heat insulator encloses the heater and the lower portion of the heat conductor, so that a bottom-up gradient temperature field is formed in the heat conductor.

The beneficial effects of the present invention are as below: as the internal microstructure of the NiTi alloy root canal file with a flexibility gradient gradually changes along the axial direction and its strength also gradually changes, its flexibility and strength show gradient change along the axial direction of the root canal file, with a flexibility gradient, an excellent cutting property and a high anti-fatigue life, which significantly improves the operation performance, safety and life of the root canal files.

DETAILED DESCRIPTION OF THE PREFERRED EMBODIMENTS

The present invention is further detailed in combination with the drawings and embodiments as follows.

Figure 1:
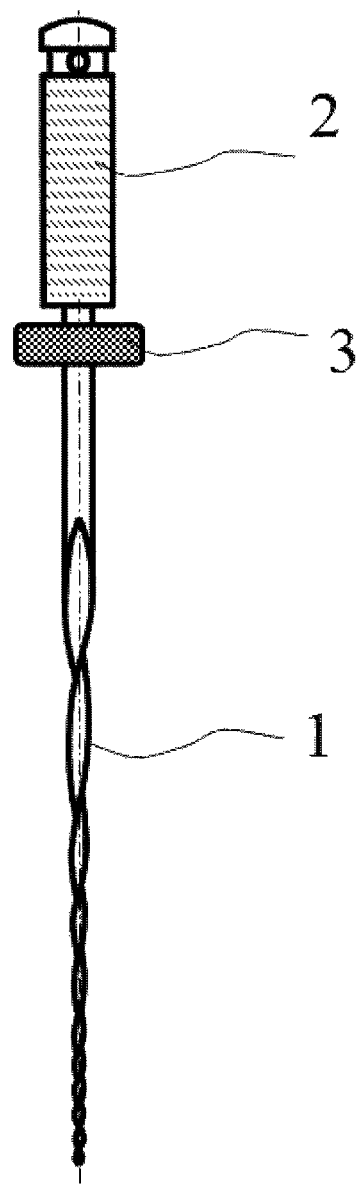
FIG. 1 illustrates the structure of the root canal file in the prior art.
Figure 2:
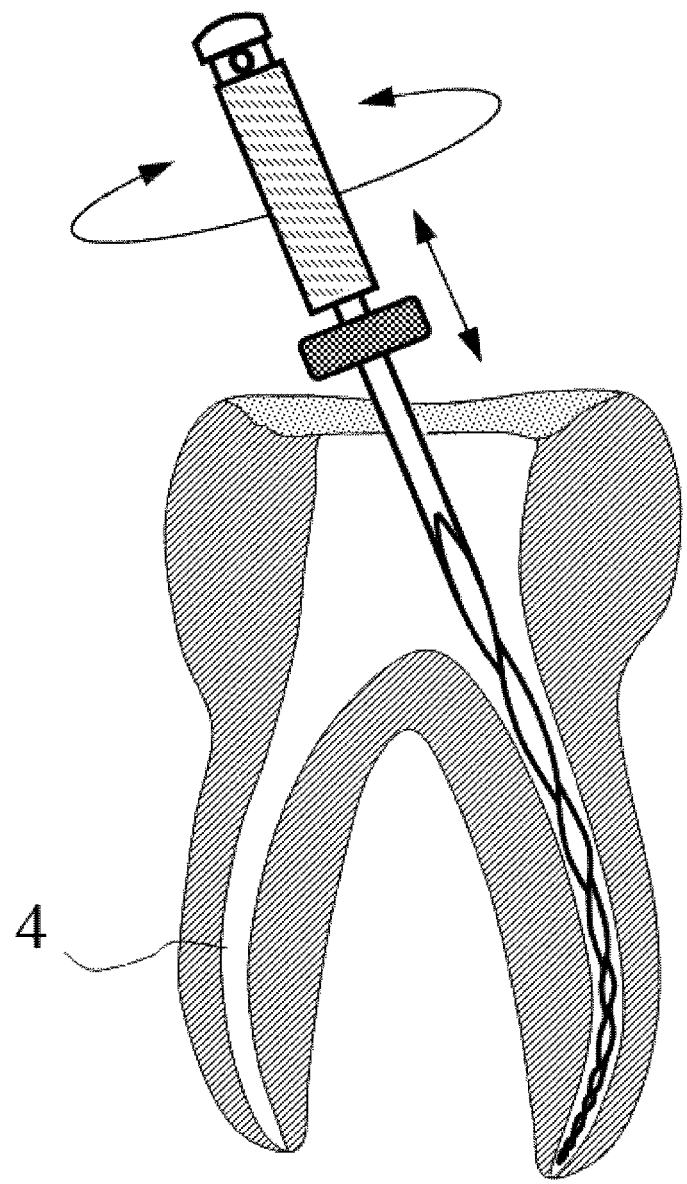
FIG. 2 illustrates the working principle of the root canal file in the prior art.
Figure 3:
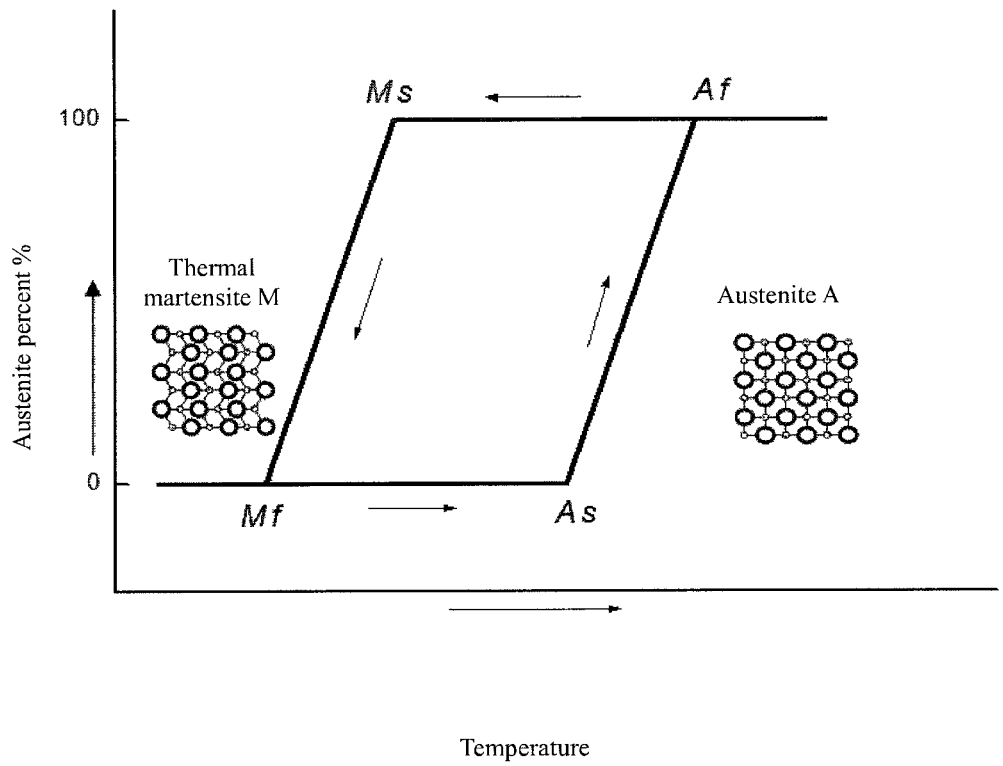
FIG. 3 illustrates the phase transition of thermal martensite in the NiTi alloy in the prior art.
Figure 4:
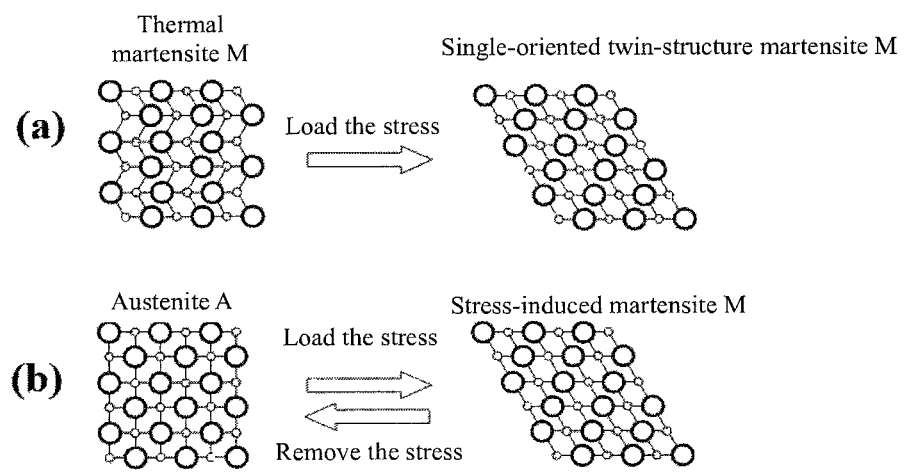
FIG. 4 illustrates the internal structure of martensite (a) and austenite (b) and the deformation thereof.
Figure 5:
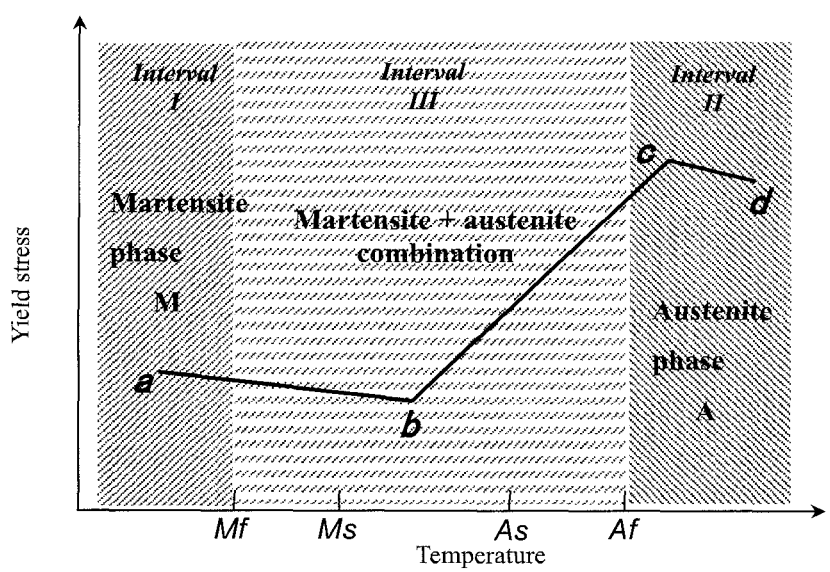
FIG. 5 illustrates the relationship between the yield stress of the NiTi alloy and the deformation temperature.
Figure 6:
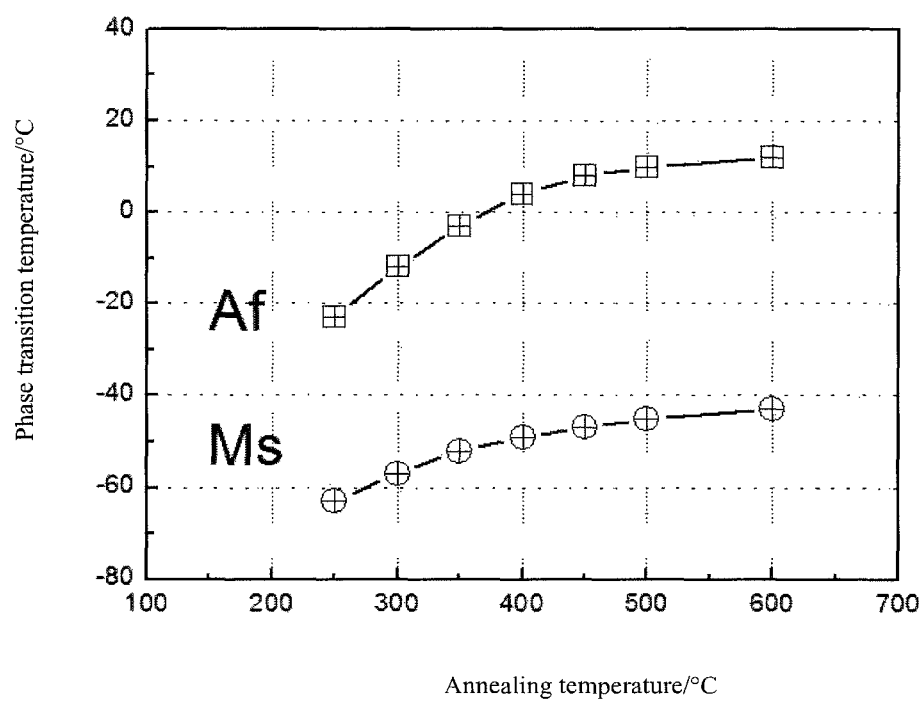
FIG. 6 illustrates the relationship between the phase transition temperature and the annealing temperature of the cold-deformation NiTi alloy.
Figure 7:
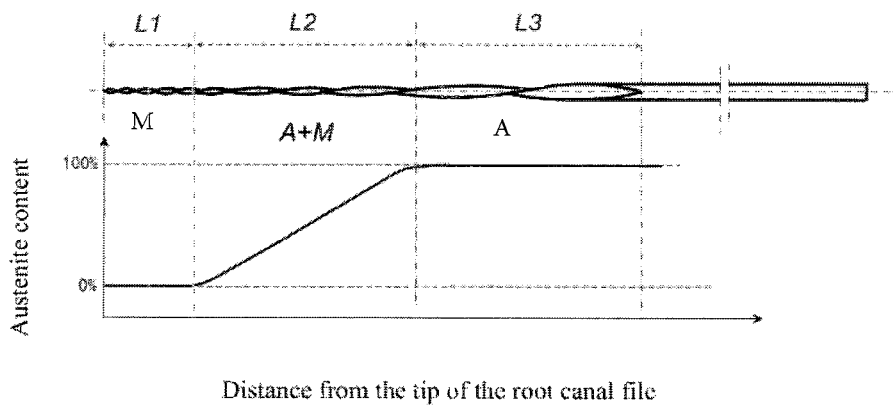
FIG. 7 illustrates the changes in the distance from each phase of microstructure of the NiTi alloy root canal file with a flexibility gradient in the present invention to the tip of the root canal file.

As shown in FIG. 5 to FIG. 10, for a NiTi alloy root canal file with a flexibility gradient, referred to as root canal file, the internal microstructure of the root canal file changes from the tip along the length of the root canal file under the operation temperature (37° C.) of the root canal file, and in the tip section L1, the internal microstructure is martensite M, with the Ms of this section of alloy higher than 37° C.; in the rear section L3 of the root canal file, the internal microstructure is austenite A, with the Af of this section of alloy higher than 37° C.; in the middle section L2, the internal microstructure of the root canal file is combined martensite M and austenite A (M+A), and the microstructure of martensite M is continuously reduced and the microstructure of austenite A is continuously increased as the distance from the tip increases, as shown in FIG. 7.

In the tip's Section L1, the internal microstructure is martensite M, which gives the section low strength while excellent flexibility so as to lead the root canal file to the tip of the root canal smoothly and effectively prevent the generation of steps and lateral perforation on the inner wall of the root canal; in Section L2, the internal microstructure is combined martensite M and austenite A and the changes in the microstructure gradually vary, which gives the section a certain strength and appropriate flexibility to meet the requirement of effectively removing diseased tissues and complete root canal shaping; in the rear Section L3 of the root canal file, the microstructure is austenite A which gives the section higher strength and excellent cutting property. In Section L1 and L2 of such a root canal file, the microstructure is martensite M or the combined martensite M and austenite A, which gives the section a higher anti-fatigue fracture property.

As the internal microstructure of such a root canal file gradually changes along the axial direction of the root canal file and its strength also gradually changes, its flexibility and strength show gradient change along the axial direction of the root canal file.

The NiTi alloy root canal file with a flexibility gradient is manufactured in such a way: the NiTi alloy wire which has been machined to a super-elastic state is taken as a raw material. The Ni content of the alloy shall be higher than 50.6 at % Ni (atomic ratio), and the alloy needs to be cold-drawn to be wires of a certain diameter and the deformation of the cold drawing should be 35-45%. The cold-drawn wires are annealed and straightened at 450-600° C. for 30-120 min to obtain raw materials for the root canal file with a flexibility gradient. The Af temperature of the NiTi alloy wires is controlled at 0-30° C.

Figure 8:
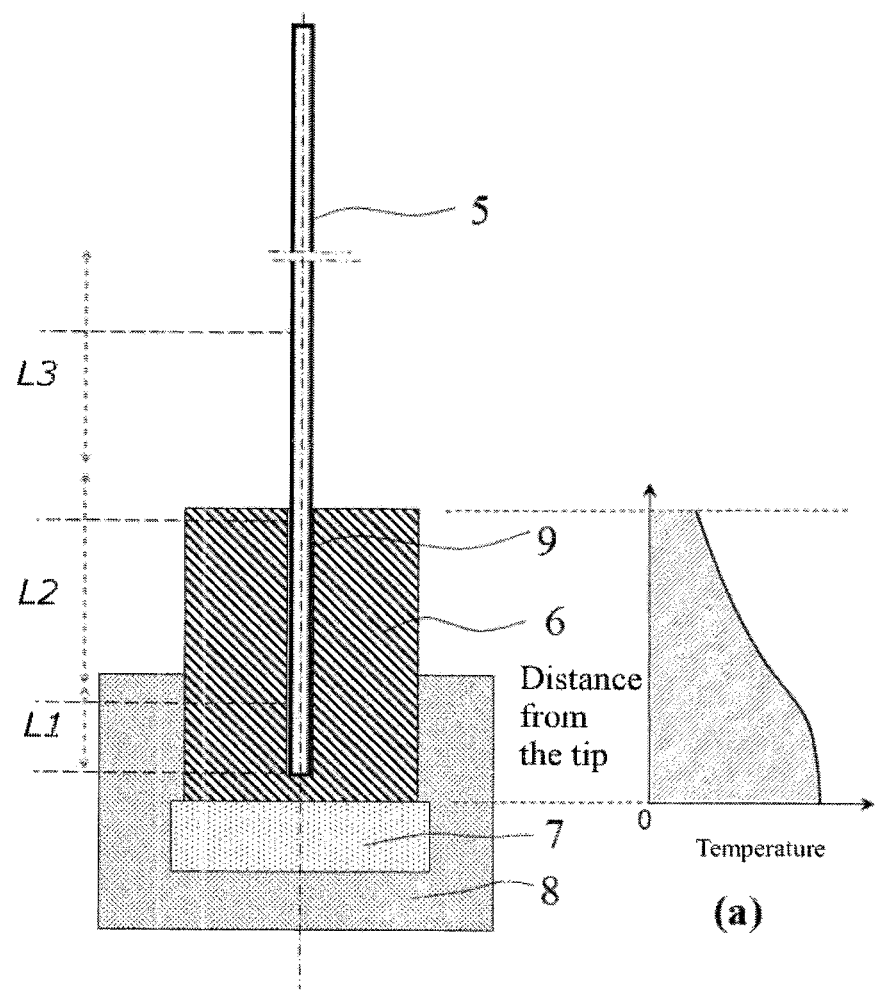
FIG. 8 illustrates the root canal file blank and the flexibility gradientization unit as well as the temperature field.

A manufacturing method for the NiTi alloy root canal file with a flexibility gradient is that the raw materials above are machined to prepare a root canal file blank 5 of a certain length, and the root canal file blank 5 is treated on a flexibility gradientization unit for a flexibility gradient as shown in FIG. 8.

The flexibility gradientization unit comprises a heat conductor 6, an electric heater 7 and a heat insulator 8, wherein a hole 9 is made in the heat conductor, and the root canal file blank 5 is inserted in the hole 9. The lower portion of the heat conductor 6 is snugly mounted with an electric heater 7, and a heat insulator 8 encloses the heater 7 and the lower half of the heat conductor 6 to prevent heat loss from the bottom, so that a bottom-up gradient temperature field is formed inside the heat conductor 6, as shown in FIG. 8(a).

The annealing can change the phase-transition temperature of the NiTi alloy, as shown in FIG. 6. The blank 5 is inserted in the hole 9 of the heat conductor 6, and the blank 5 is heated by way of heat conduction. Further, since there is a continuously changing temperature field in the heat conductor 6, the heating temperatures of all points of the blanks 5 are different. By way of properly designing the shape of the heat conductor 6 and controlling the temperature of the electric heater 7, it is possible to change the arrangement of the temperature field in the heat conductor 6 so that the heating temperature at each point of the blank 5 can reach the desired requirement. By way of controlling the heating time, it is possible that under the operation temperature (37° C.) of the root canal file, the microstructure in Section L1 of the blank 5 is martensite M, the microstructure in Section L3 is austenite A and the microstructure in Section L2 is combined martensite M and austenite A (M+A), and the contents of martensite M and austenite A continuously change as the distance from the tip increases.

Figure 9:
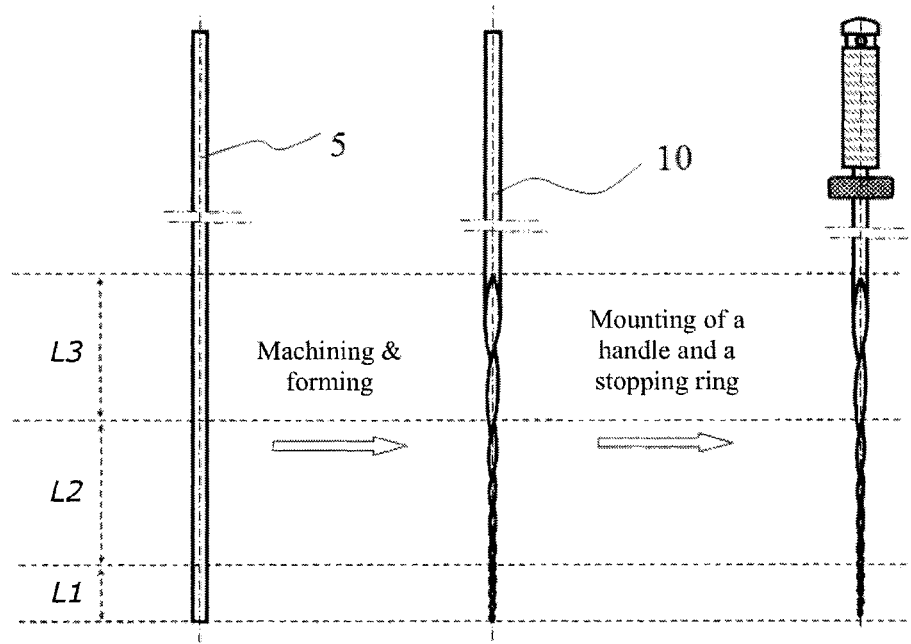
FIG. 9 illustrates the root canal file blank and the root canal file needle.
Figure 10:
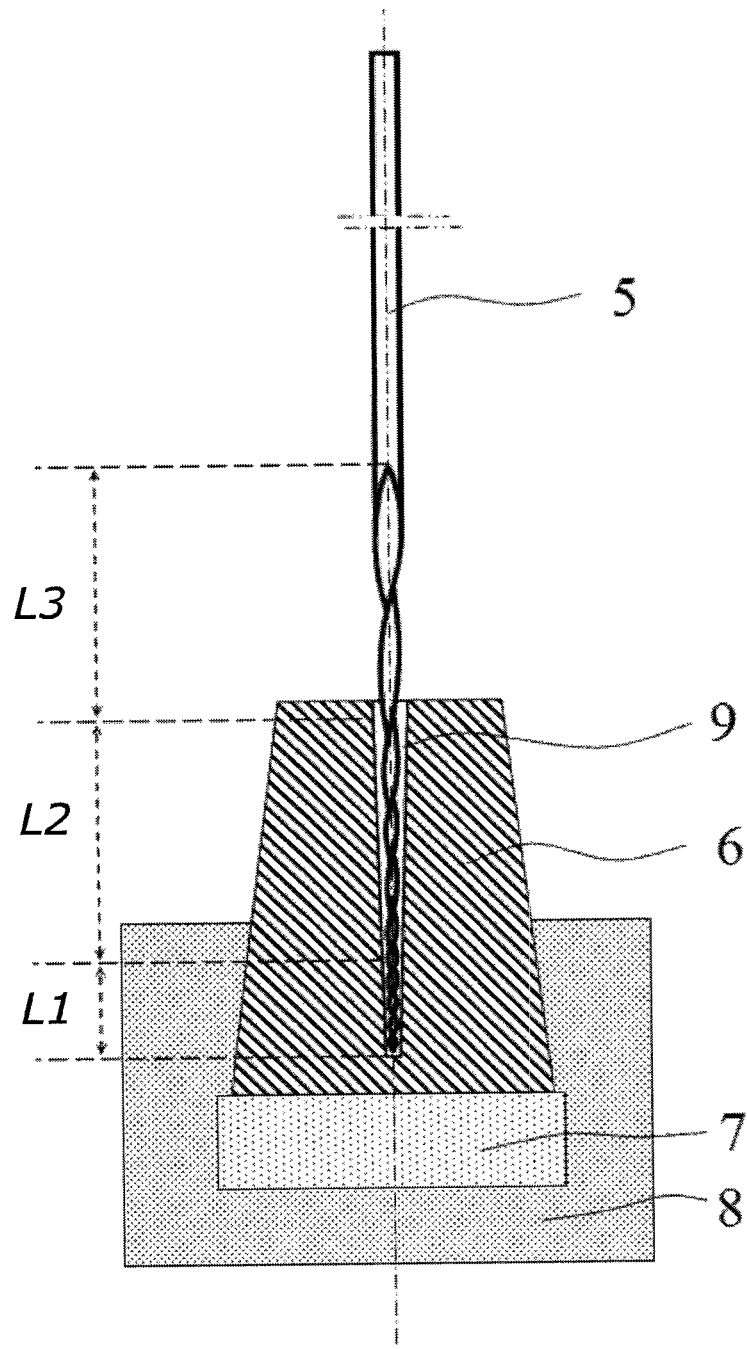
FIG. 10 illustrates the root canal file needle and the flexibility gradientization unit.

After flexibility gradientization, the root canal file blank 5 is machined to obtain the required root canal file needle 10, as shown in FIG. 9. The root canal file needle 10 is then mounted on a handle 2 and a stopping ring 3 to form a NiTi alloy root canal file with a flexibility gradient as described in the present invention.

Another manufacturing method for the NiTi alloy root canal file with a flexibility gradient is that the super-elastic NiTi alloy wire is machined to a root canal file needle 10. The formed root canal file needle 10 is inserted in the flexibility gradientization unit for treatment, as shown FIG. 10. The hole 9 in the heat conductor 6 may be profiled and the shape of the heat conductor 6 may be of conical or other shapes.

After the flexibility gradientization, the root canal file needle 10 is mounted on a handle 2 and a stopping ring 3 to form a NiTi alloy root canal file with a flexibility gradient as described in the present invention.

The arrangement of the temperature field inside the flexibility gradientization unit can reach the requirement by way of changing the shape of the heat conductor 6, and the shape of the heat conductor 6 may be of cylindrical, conical or other shapes, while the hole 9 in the heat conductor 6 may be of a cylindrical or profiled shape.

The flexibility gradientization unit can realize the flexibility gradientization of the root canal file blank 5 or the root canal needle 10 through control of technological parameters such as the temperature of the heat conductor 6 and the heating time.

For a manufacturing method for the NiTi alloy root canal file with a flexibility gradient, as the internal microstructure of the NiTi alloy root canal file with a flexibility gradient gradually changes along the axial direction and its strength gradually changes, its flexibility and strength show gradient change along the axial direction of the root canal file, with a gradient flexibility, an excellent cutting property and a high anti-fatigue life, which significantly improves the operation performance, safety and life of the root canal files.

The foregoing are further detailed for the present invention in combination with detailed preferable embodiments, but are not intended to limit detailed embodiments of the present invention. Those skilled in the art can make a variety of simple deductions or variations without deviating from the principle of the present invention, and all these should be covered in the protection scope of the present invention.

What is claimed is:

1. A NiTi alloy root canal file with a flexibility gradient, comprising:
    a tip;
    a middle portion; and
    a rear portion, the tip, the middle portion and the rear portion being divided along a longitudinal direction,
    wherein an internal microstructure of the tip is martensite, an internal microstructure of the rear portion is austenite and an internal microstructure of the middle portion is a combined microstructure of martensite and austenite, and
    wherein the microstructure of martensite is continuously reduced and the microstructure of austenite is continuously increased as the distance from the tip increases.

2. A manufacturing method for the NiTi alloy root canal file with a flexibility gradient, that the method comprising:
    preparing a super-elastic NiTi alloy wire with a high content of Ni as a raw material, said preparing comprising:
        cold-drawing a super-elastic NiTi alloy to form the super-elastic NiTi alloy wire;
        annealing the super-elastic NiTi alloy wire; and
        straitening the super-elastic NiTi alloy wire;
    preparing root canal file blanks of a certain length using the raw material;
    subjecting the root canal file blanks to a flexibility gradientization treatment in a flexibility gradientization unit to prepare root canal file blanks with a flexibility gradient;
    machining the root canal file blanks with a flexibility gradient to prepare root canal file needles with a flexibility gradient; and
    after the flexibility gradientization, mounting the root canal file needle on a handle and a stopping ring to form a NiTi alloy root canal file with a flexibility gradient.

3. A manufacturing method for the NiTi alloy root canal file with a flexibility gradient, that the method comprising:
    taking a super-elastic NiTi alloy wire with a high content of Ni as a raw material;
    paring root canal file blanks of a certain length using the raw material;
    subjecting the root canal file blanks to a flexibility gradientization treatment in a flexibility gradientization unit to prepare root canal file blanks with a flexibility gradient;
    machining the root canal file blanks with a flexibility gradient to prepare root canal file needles with a flexibility gradient; and
    after the flexibility gradientization, mounting the root canal file needle on a handle and a stopping ring to form a NiTi alloy root canal file with a flexibility gradient,
    wherein the flexibility gradientization unit comprises:
        a heat conductor;
        an electric heater; and
        a heat insulator,
    wherein the electric heater is provided in the heat insulator, the heat conductor is provided on the electric heater, a hole used for heating the root canal file blanks or the root canal file needles is made on the heat conductor, the lower portion of the heat conductor is snugly mounted with the electric heater, and the heat insulator encloses the heater and the lower portion of the heat conductor, so that a bottom-up gradient temperature field is formed in the heat conductor.

4. A manufacturing method for the NiTi alloy root canal file with a flexibility gradient, the method comprising:
    preparing a super-elastic NiTi alloy wire with a high content of Ni as a raw material, said preparing comprising:
        cold-drawing a super-elastic NiTi alloy to form the super-elastic NiTi alloy wire;
        annealing the super-elastic NiTi alloy wire; and
        straitening the super-elastic NiTi alloy wire;
    machining the raw material to prepare the root canal file needles;
    then inserting the root canal file needles in a flexibility gradientization unit for treatment to prepare root canal file needles with a flexibility gradient; and
    mounting the root canal file needles with a flexibility gradient on a handle and a stopping ring to form a NiTi alloy root canal file with a flexibility gradient.

5. A manufacturing method for the NiTi alloy root canal file with a flexibility gradient, the method comprising:
    taking a super-elastic NiTi alloy wire with a high content of Ni as a raw material;
    machining the raw material to prepare the root canal file needles;
    then inserting the root canal file needles in a flexibility gradientization unit for treatment to prepare root canal file needles with a flexibility gradient; and mounting the root canal file needles with a flexibility gradient on a handle and a stopping ring to form a NiTi alloy root canal file with a flexibility gradient,
wherein the flexibility gradientization unit comprises:
a heat conductor;
an electric heater; and
a heat insulator,
wherein the electric heater is provided in the heat insulator, the heat conductor is provided on the electric heater, a hole used for heating the root canal file blanks or the root canal file needles is made on the heat conductor, the lower portion of the heat conductor is snugly mounted with the electric heater, and the heat insulator encloses the heater and the lower portion of the heat conductor, so that a bottom-up gradient temperature field is formed in the heat conductor.

* * * * *